(12) United States Patent
Nelson

(10) Patent No.: US 7,331,341 B2
(45) Date of Patent: Feb. 19, 2008

(54) LIVING SPECIMEN INDUCTION CHAMBER

(75) Inventor: Michael Bo Nelson, San Francisco, CA (US)

(73) Assignee: Xenogen Corporation, Alameda, CA (US)

( * ) Notice: Subject to any disclaimer, the term of this patent is extended or adjusted under 35 U.S.C. 154(b) by 842 days.

(21) Appl. No.: 10/370,031

(22) Filed: Feb. 19, 2003

(65) Prior Publication Data
US 2003/0209244 A1  Nov. 13, 2003

Related U.S. Application Data

(63) Continuation-in-part of application No. 10/081,040, filed on Feb. 20, 2002.

(60) Provisional application No. 60/385,397, filed on May 31, 2002.

(51) Int. Cl.
*A61M 16/00* (2006.01)
*A01K 1/00* (2006.01)

(52) U.S. Cl. ............... 128/203.12; 128/203.14; 119/416

(58) Field of Classification Search ......... 128/202.12, 128/200.24, 203.12, 203.14, 204.18, 204.21, 128/205.18, 205.26, 202.16, 203.17, 203.26; 119/416–421; 600/21, 22
See application file for complete search history.

(56) References Cited

U.S. PATENT DOCUMENTS

| | | | |
|---|---|---|---|
| 3,794,027 A | 2/1974 | Johnson | |
| 4,520,808 A | 6/1985 | La Bauve | |
| 4,582,055 A * | 4/1986 | McDougal et al. | .... 128/202.12 |
| 4,721,060 A | 1/1988 | Cannon et al. | |
| 4,917,046 A * | 4/1990 | Spengler | ............... 119/420 |
| 5,202,091 A | 4/1993 | Lisenbee | |
| 5,297,502 A * | 3/1994 | Jaeger | ................. 119/420 |
| 5,319,209 A | 6/1994 | Miyakawa et al. | |
| 5,414,258 A | 5/1995 | Liang | |
| 5,636,299 A | 6/1997 | Bueno et al. | |

(Continued)

FOREIGN PATENT DOCUMENTS

| | | |
|---|---|---|
| EP | 0 097 060 | 12/1983 |
| WO | WO 00/17643 | 3/2000 |

OTHER PUBLICATIONS

Hamamatsu Corporation, USA, website, http://usa.hamamatusu.com/ pp. 1-4, Apr. 27, 2001, printed on Apr. 27, 2001.

(Continued)

*Primary Examiner*—Teena Mitchell
(74) *Attorney, Agent, or Firm*—Beyer Weaver LLP

(57) ABSTRACT

The invention described herein provides an induction chamber used to sedate one or more living specimens. The induction chamber comprises at least one gas inlet through which anesthesia gas and oxygen are supplied. To minimize escape of anesthetizing gas is into the ambient room or surroundings, the induction chamber includes a gas outlet or port that draws anesthesia gas. The induction chamber also comprises a device that obstructs gas flow through the gas outlet based on the position of the door. In one chamber design, when the door closes, the gas outlet is blocked. Thus, opening the door to the induction chamber causes anesthesia gas is to be drawn through the outlet while closing the door allows anesthesia gas to collect in the chamber and sedate any specimens located therein.

23 Claims, 6 Drawing Sheets

U.S. PATENT DOCUMENTS

| | | | |
|---|---|---|---|
| 5,637,874 | A | 6/1997 | Honzawa et al. |
| 5,650,135 | A | 7/1997 | Contag et al. ............... 424/9.1 |
| 5,705,807 | A | 1/1998 | Throngnumchai et al. |
| 5,738,101 | A | 4/1998 | Sappey |
| 5,840,572 | A | 11/1998 | Copeland et al. |
| 5,867,250 | A | 2/1999 | Baron |
| 5,964,220 | A | 10/1999 | Boussignac et al. |
| 5,970,164 | A | 10/1999 | Bamberger et al. |
| 6,217,847 | B1 | 4/2001 | Contag et al. |
| 6,242,743 | B1 | 6/2001 | DeVito et al. |
| 6,321,111 | B1 | 11/2001 | Perelman et al. |
| 6,352,076 | B1* | 3/2002 | French .................. 128/203.12 |
| 6,364,829 | B1 | 4/2002 | Fulghum |
| 6,615,063 | B1 | 9/2003 | Ntziachristos et al. |
| 6,775,567 | B2 | 8/2004 | Cable et al. |
| 6,776,158 | B1 | 8/2004 | Anderson et al. |
| 6,904,912 | B2* | 6/2005 | Roy et al. .............. 128/203.18 |
| 7,213,538 | B2* | 5/2007 | Han et al. ................... 119/752 |
| 7,252,050 | B2* | 8/2007 | Cole .......................... 119/416 |
| 2007/0089742 | A1 | 4/2007 | Dalgetty et al. |
| 2007/0091428 | A1 | 4/2007 | Wilson et al. |

OTHER PUBLICATIONS

Hamamatsu, Imaging Box Instruction Manual, 55310-224-1, Nov. 2000. Hamamatsu Corporation, USA, website, http://usa.hamamatusu.com/ pp. 1-.

Dosch, Michael P. CRNA MS, "The Anesthesia Gas Machine, Vaporizers, Compressed Gases, Safety: Avoiding the Pitfalls" http://ourworld-top.cs.com/doschm/agmpart1.htm ,http://www.gasnet.org/education/machine Copyright. Last revised Aug. 27, 2000.

Smith, Jennifer C., DVM, Brad Bolon, DVM, S, PHD, Diplomate, ACVP, Diplomate, ABT "Atmospheric Waste Isoflurane Concentrations Using Conventional Equipment and Rat Anesthesia Protocols", vol. 41 No. 2, Mar. 2002.

Weigel, Wade "The Intranet in your palm", Penn State Anesthesiology: Anesthesia Scavenging Systems, Mar. 29, 2001, pp. 1-3.

Horne, et al., "A Nonrebreathing Anesthetic Delivery System for Mice", Lab Animal Magazine, vol. 27, No. 7, Aug. 4, 1997.

J. B. Mulder, "A Unit for Inhalation Anesthesia of Small Laboratory Animals", Anesthesia and Anelgesia, May-Jun. 1973, vol. 52, No. 3, pp. 369-372.

Michael Rand, "Handling, Restraint, and Techniques of Laboratory Rodents", May 2001, Department of Animal Care, University of Arizona.

Office Action dated Jan. 19, 2007 in U.S. Appl. No. 10/081,040.

Office Action dated May 24, 2007 in U.S. Appl. No. 10/081,040.

Office Action dated Jun. 13, 2007 in U.S. Appl. No. 11/567,613.

Office Action dated Oct. 16, 2006 in U.S. Appl. No. 10/081,040.

Office Action in U.S. Appl. No. 11/567,613 (XENOP008D2) dated Jun. 13, 2007.

* cited by examiner

US 7,331,341 B2

LIVING SPECIMEN INDUCTION CHAMBER

CROSS-REFERENCE TO RELATED APPLICATION

This application claims priority under 35 U.S.C. §119(e) from co-pending U.S. Provisional Patent Application No. 60/385,397 filed on May 31, 2002, which is herein incorporated by reference for all purposes; this application is also a continuation-in-part of U.S. patent application entitled "Multiple Output Anesthesia System" by Richard George Dalgetty et al., filed on Feb. 20, 2002 (U.S. application Ser. No. 10/081,040), which is herein incorporated by reference herein for all purposes.

FIELD OF THE INVENTION

The present invention relates generally to anesthesia delivery systems and imaging systems. In particular, the present invention relates to induction chambers used to anesthetize mammalian specimens in imaging and research applications.

BACKGROUND OF THE INVENTION

One new and specialized type of imaging involves the capture of low intensity light—often on the order of only tens to hundreds of photons—from a light-emitting sample. The low intensity light source may be emitted from any of a variety of light-emitting sources within a living specimen, e.g., luciferase expressing cells within a mouse. The source of the light indicates portions of the sample, such as traced molecules in a particular portion of a mammalian specimen, where an activity of interest may be taking place. Some specialized in-vivo imaging applications include analysis of one or more representations of emissions from internal portions of a specimen superimposed on a photographic representation of the specimen. The photographic representation provides the user with a pictorial reference of the specimen. The luminescence representation indicates portions of the specimen where an activity of interest may be taking place.

Obtaining a luminescence representation often involves image capture over an extended period of time, e.g., minutes, in a specialized imaging box. The imaging box is a custom-made apparatus designed to tightly control the amount of light in the box and minimize light entering from the surrounding room. The living specimen is typically anesthetized during imaging to prevent movement that may affect prolonged image capture.

An induction chamber is typically used to anesthetize the living specimen before being placed in the imaging box. A laboratory technician or researcher places one or more conscious living specimens in the induction chamber. A combination of anesthetizing gas and oxygen is then supplied to the induction chamber. The specimen remains in the induction chamber until it loses consciousness, or is similarly sedated, and is then transported by the laboratory technician into the imaging box. Transporting living specimens in and out of the induction chamber may allow the anesthesia gas to escape into the ambient surroundings. Preferably, the amount of anesthesia gas that escapes is minimized.

Conventional induction chambers rely on a purge system to manage anesthesia gas escape. The purge system forces high-pressure oxygen into the induction chamber before the door or user access is opened. A passive exhaust port leading from the induction chamber interior receives the high-pressure purge oxygen and any gases present in the induction chamber before the purge. One problem with purge systems is that the high burst of oxygen, and/or removal of all anesthetizing gas, frequently awakens any living specimens in the induction chamber. When a single living specimen is in the induction chamber, this is clearly defeating to the intended induction chamber purpose. Lab technicians however often work with multiple living specimens at a single time and purging the induction chamber to remove one specimen may then lead to more than one specimen awakening.

In view of the foregoing, an improved induction chamber capable of anesthetizing one or more living specimens would be desirable.

SUMMARY OF THE INVENTION

The present invention relates to an induction chamber used to sedate one or more living specimens. The induction chamber comprises at least one gas inlet through which anesthesia gas and oxygen are supplied. To minimize escape of anesthetizing gas is into the ambient room or surroundings, the induction chamber includes a gas outlet or port that draws anesthesia gas. A negative or vacuum pressure is applied to the gas outlet. The negative pressure draws gases from within the induction chamber, and may draw gases from the ambient surroundings around the induction chamber when a door allowing a lab technician access to the induction chamber interior opens. The induction chamber also comprises a device that obstructs gas flow through the gas outlet based on the position of the door. In one embodiment, when the door closes, the gas outlet is blocked. Thus, opening the door to the induction chamber causes anesthesia gas is to be drawn through the outlet while closing the door allows anesthesia gas to collect in the chamber and sedate any specimens located therein. The induction chamber is particularly useful for sedating a living specimen prior to insertion in an imaging box or chamber.

In one embodiment, the gas outlet is near the door. In a specific embodiment where the door is on the top portion of the chamber, the gas outlet is vertically disposed on the top half of the induction chamber. In this case, suction of anesthesia gas removes a top layer of anesthesia gas from a top portion of the induction chamber interior cavity. One or more living specimens resting on the bottom half of the induction chamber interior cavity are thus still exposed to anesthesia gas while the door is open. This allows the lab technician to remove one or more specimens without awakening the other living specimens.

In one aspect, the present invention relates to an induction chamber for delivering anesthesia gas to a living specimen. The induction chamber comprises a set of walls defining an interior cavity. The induction chamber also comprises a door that is movable between an opened condition that enables gaseous communication between the interior cavity and the environment exterior to the induction chamber through an opening, and a closed condition that seals the interior cavity from the environment exterior to the induction chamber. The induction chamber further comprises a gas inlet disposed in one of the set of walls and capable of providing anesthesia gas to the interior cavity. The induction chamber additionally comprises a gas outlet disposed in one of the set of walls and capable of drawing anesthesia gas from the interior cavity when the door is in the opened condition. The induction chamber also comprises a gas outlet obstruction that varies flow of anesthesia gas from the interior cavity through the gas outlet based on the position of the door.

In another aspect, the present invention relates to a method of using an induction chamber. The induction chamber comprises a set of walls that define an interior cavity. The induction chamber also comprises a door that is movable between an opened condition and a closed condition. The method comprises supplying an anesthesia gas into the interior cavity. The method also comprises drawing anesthesia gas through a gas outlet disposed on one of the set of walls when the door is in the opened condition. The method further comprises obstructing gas flow through the gas outlet when the door is in the closed condition.

In yet another aspect, the present invention relates to an imaging system for capturing an image of a living specimen with a camera. The system comprises an imaging box having a set of walls enclosing an interior cavity and a camera mount configured to position the camera to view the living specimen in the interior cavity while the living specimen is anesthetized. The system comprises an induction chamber. The induction chamber comprises a set of walls defining an interior cavity. The induction chamber also comprises a door that is movable between an opened condition that enables gaseous communication between the interior cavity and the environment exterior to the induction chamber through an opening, and a closed condition that seals the interior cavity from the environment exterior to the induction chamber. The induction chamber further comprises a gas inlet disposed in one of the set of walls and capable of providing anesthesia gas to the interior cavity. The induction chamber additionally comprises a gas outlet disposed in one of the set of walls and capable of drawing anesthesia gas from the interior cavity when the door is in the opened condition. The induction chamber also comprises a gas outlet obstruction that varies flow of anesthesia gas from the interior cavity through the gas outlet based on the position of the door.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

In the following detailed description of the present invention, numerous specific embodiments are set forth in order to provide a thorough understanding of the invention. However, as will be apparent to those skilled in the art, the present invention may be practiced without these specific details or by using alternate elements or processes. In other instances well known processes, components, and designs have not been described in detail so as not to unnecessarily obscure aspects of the present invention.

I. Imaging System

Figure 1:
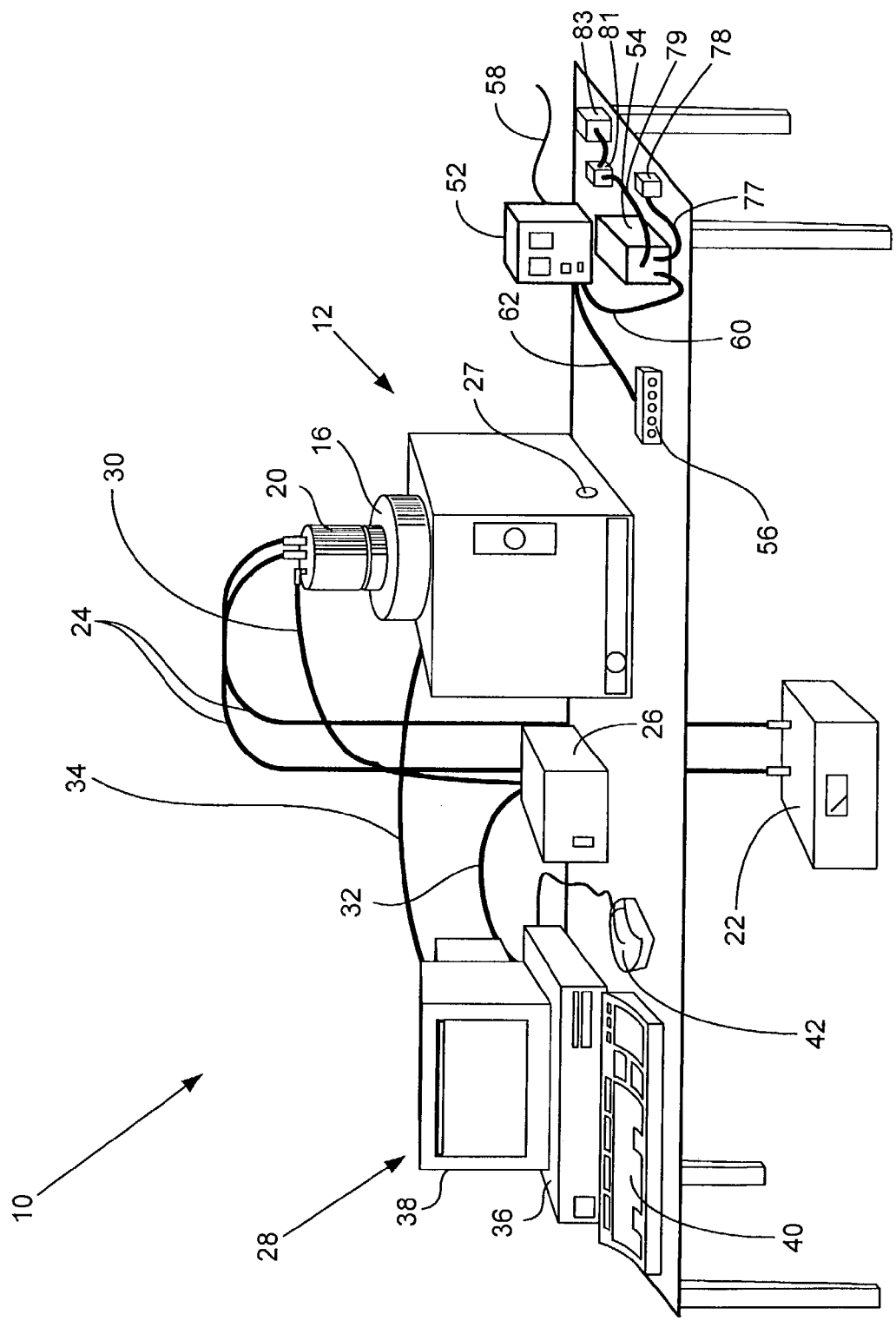
FIG. 1 is a perspective view of an imaging system in accordance with one embodiment of the present invention.

In one aspect, the present invention relates to imaging systems for capturing an image of a low intensity light source. FIG. 1 illustrates an imaging system 10 configured to capture photographic and luminescence images in accordance with one embodiment of the present invention. Imaging system 10 may be used for imaging a low intensity light source, such as luminescence from luciferase-expressing cells, fluorescence from fluorescing molecules, and the like. The low intensity light source may be emitted from any of a variety of light-emitting samples which may include, for example, animals containing light-emitting molecules, e.g., various mammalian subjects such as mice containing luciferase expressing cells.

Imaging system 10 comprises an imaging box 12 having a door and walls that define an interior cavity that is adapted to receive a light-emitting sample in which low intensity light, e.g., luciferase-based luminescence, is to be detected. Imaging box 12 is often referred to as "light-tight", e.g., it seals out essentially all of the external light from the ambient room from entering the box 12, and may include one or more seals that prevent light passage into the box when the door is closed. The seals may also be effective to prevent anesthesia gases used within box 12 from escaping into the ambient room. Imaging box 12 is suitable for imaging including the capture of low intensity light on the order of individual photons, for example.

Imaging box 12 includes an upper housing 16 adapted to receive a camera. A high sensitivity camera 20, e.g., an intensified or a charge-coupled device (CCD) camera, is mounted on top of upper housing 16 and positioned above imaging box 12. CCD camera 20 is capable of capturing luminescent and photographic (i.e., reflection based images) images of a sample placed within imaging box 12. CCD camera 20 is cooled by a suitable source such as a refrigeration device 22 that cycles a cryogenic fluid through the CCD camera via conduits 24. A suitable refrigeration device is the "CRYOTIGER" compressor, which can be obtained from IGC-APD Cryogenics Inc., Allentown, Pa. Other methods, such as liquid nitrogen, may be used to cool CCD camera 20. Imaging system 10 also includes an anesthesia delivery system that delivers anesthesia gas and oxygen. The anesthesia delivery system includes console 52, induction chamber 54 (FIGS. 2A-2D), and a gas delivery device 56. Console 52 allows a user or lab technician to control flow of anesthesia gas and oxygen from one or more gas outlets on the console. The output of console 52 is a combination of low-pressure oxygen and anesthesia gas. As shown, console 52 includes two gas delivery outlets: a first gas delivery outlet for servicing gas delivery device 56 and a second delivery outlet that services induction chamber 54.

Oxygen delivery conduit 58, such as a rubber tube or hose, is operably coupled to an oxygen inlet of main console 52 and an outlet of an oxygen supply source. For example, the oxygen supply source may be a high pressure oxygen cylinder or conventional medium pressure wall outlet. Conduit 60 is coupled to an outlet of main console 52 and coupled to inlet of induction chamber 54 and allows gaseous communication between induction chamber 54 and console 52.

Induction chamber 54 receives oxygen and anesthesia gas from conduit 60. Induction chamber 54 allows a user to anesthetize one or more living specimens that fit within induction chamber 54, and will be described in further detail with respect to FIGS. 2A-D. A passive gas outlet is included in a side wall of induction chamber 54 and coupled to conduit 77. The passive gas outlet and conduit 77 allow gases to flow passively from induction chamber 54. The gases in conduit 77 are provided to filter 78. In one embodiment, the anesthesia gas is isoflurane and filter 78 is a charcoal filter that removes unused isoflurane that passes therethrough. A filter model number 80120 F/Air Cannister as provided by A. M. Bickford of Wales Center, N.Y. is suitable for use as filter 78. Filter 78 outputs primarily oxygen. As shown, filter 78 outputs oxygen into the ambient room.

An active gas outlet is also included in a top portion of a side wall of induction chamber 54 and is coupled to conduit 79. The active gas outlet and conduit 79 actively draws gases from induction chamber 54 and provides them to filter 81. A pump 83 provides a negative pressure to the active gas outlet and conduit 79 the draws oxygen and anesthesia gas from the interior of induction chamber 54. The active gas outlet will be described in further detail below. In one embodiment, pump 83 is model number VPO125 as provided by Medo USA, of Cherry Hill, Ill.

Conduit 62 allows gaseous communication between console 52 and gas delivery device 56. Gas delivery device 56 may be placed within box 12 and includes multiple specimen interfaces for communicating anesthesia gas to one or more living specimens. For example, box 12 typically includes a stage that supports one or more mice to be imaged, and gas delivery device 56 may be place on the stage in proximity to the mice. A light-sealed hole 27 is included in a side wall of box 12 to allow a gas conduit 62 to pass therethrough while device 56 is in box 12. Conduit 62 may comprise tubing or a suitable hose. For example, ⅜ inch OD ¼ inch ID 90 durometer viton rubber tubing is suitable for use as conduits in FIG. 1.

An image-processing unit 26 optionally interfaces between camera 20 and a computer 28 through cables 30 and 32 respectively. Computer 28, which may be of any suitable type, comprises a main unit 36 that typically contains hardware including a processor, memory components such as random-access memory (RAM) and read-only memory (ROM), and disk drive components (e.g., hard drive, CD, floppy drive, etc.). Computer 28 also includes a display 38 and input devices such as a keyboard 40 and input mouse 42. Computer 28 is in communication with various components in imaging box 12 via cable 34. To provide communication and control for these components, computer 28 includes suitable processing hardware and software configured to provide output for controlling any of the devices in imaging box 12. The processing hardware and software may include an I/O card, control logic for controlling any of the components of imaging system 10, and a suitable graphical user interface that facilitates user interaction with imaging system 10. Components controlled by computer 28 may include camera 20, motors responsible for camera 20 focus, motors responsible for position control of a platform supporting the living specimens, the camera lens, f-stop, etc.

Computer 28 may also include suitable processing hardware and software for camera 20 such as additional imaging hardware and software, calibration software, and image processing logic for processing information obtained by camera 20. The logic in computer 28 may take the form of software, hardware or a combination thereof. Computer 28 also communicates with a display 38 for presenting imaging information to the user. For example, the display 38 may be a monitor, which presents an image measurement graphical user interface (GUI) that allows a user to view imaging results and also acts an interface to control the imaging system 10.

II. Induction Chamber

FIGS. 2A-2D illustrate induction chamber 54 of FIG. 1 in accordance with one embodiment of the present invention. Induction chamber 54 allows a user to anesthetize one or more living specimens that fit within induction chamber 54 and is also commonly referred to as a 'knockdown box'. Induction chamber 54 includes an interior cavity sized to receive living specimens and a gas inlet that allows a user to supply an anesthesia gas to the interior cavity, as described in greater detail below. While induction chamber 54 will now be described as an apparatus, those skilled in the area will recognize that the present invention encompasses a method of using the apparatus based on the functional components of the induction chamber.

Figure 2A:
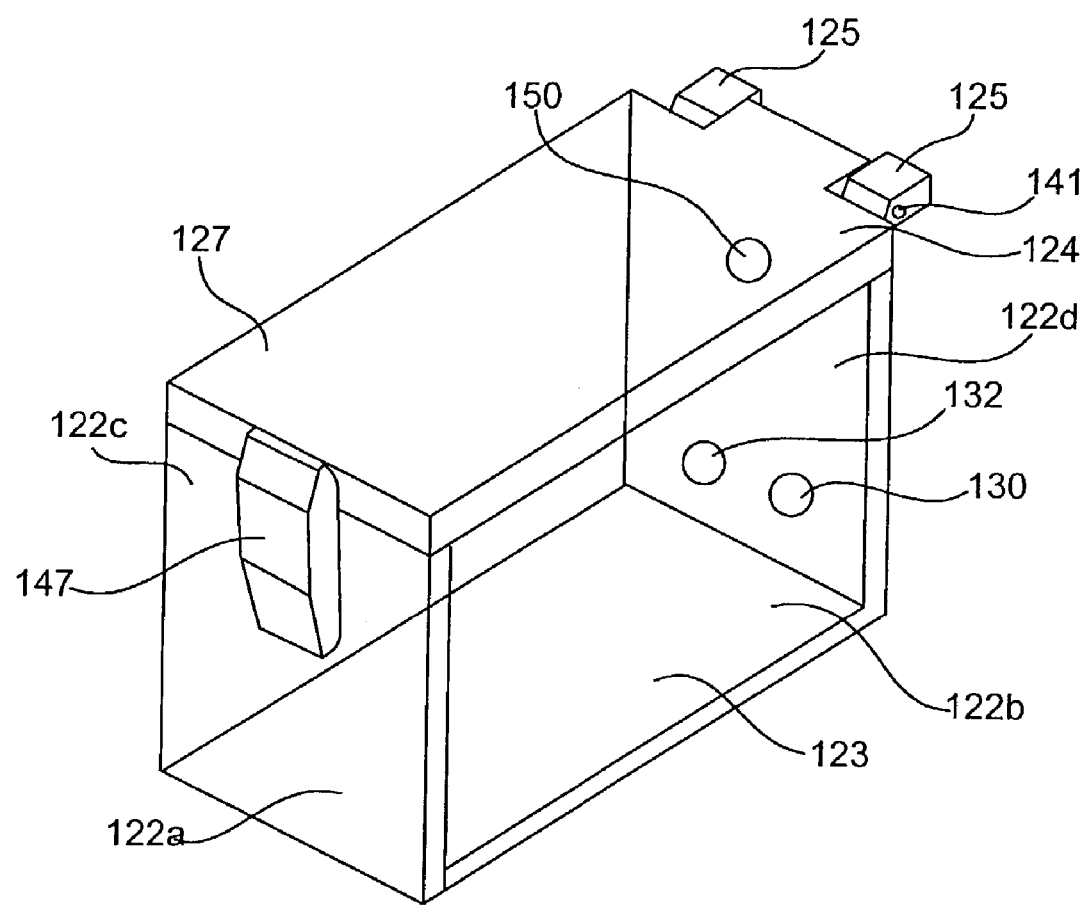
FIG. 2A illustrates a top prospective view of the front of the induction chamber of FIG. 1 in accordance with one embodiment of the present invention.
Figure 2B:
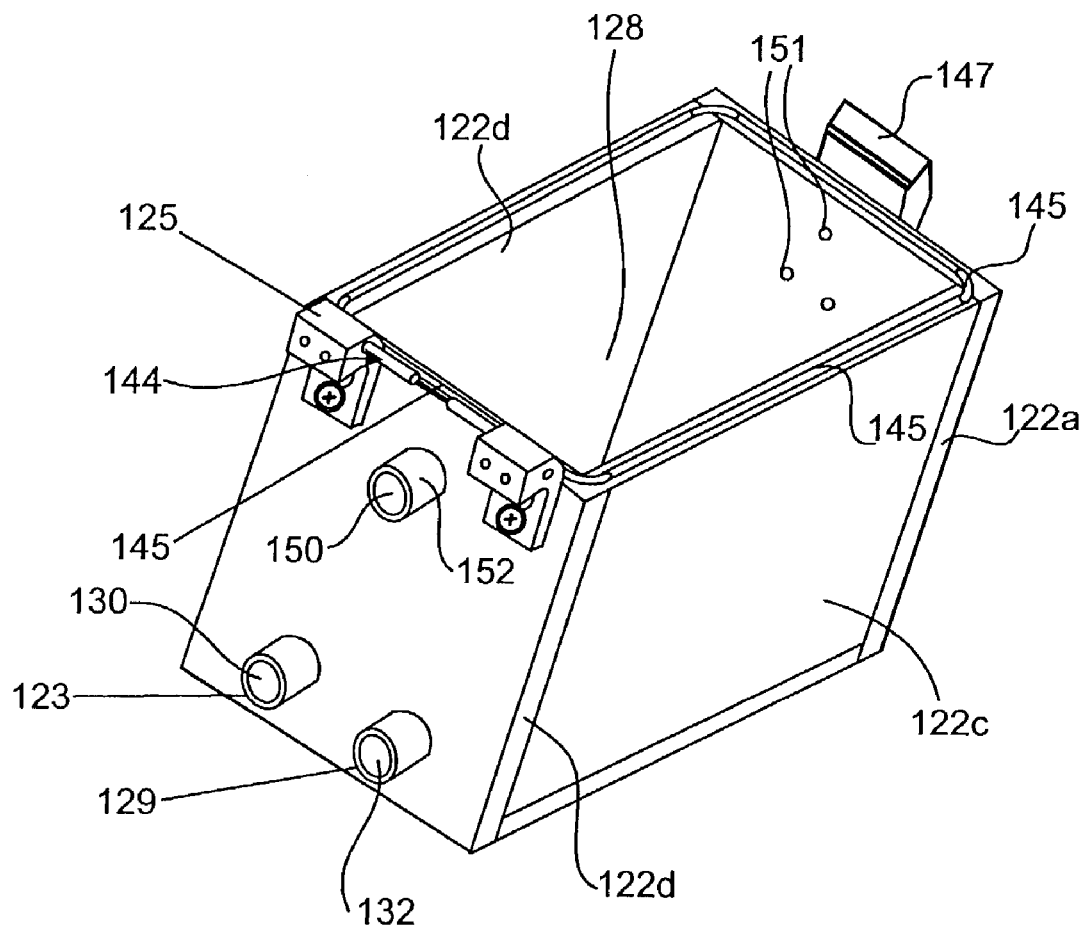
FIG. 2B illustrates a top prospective view of the back of induction chamber of FIG. 1.
Figure 2C:
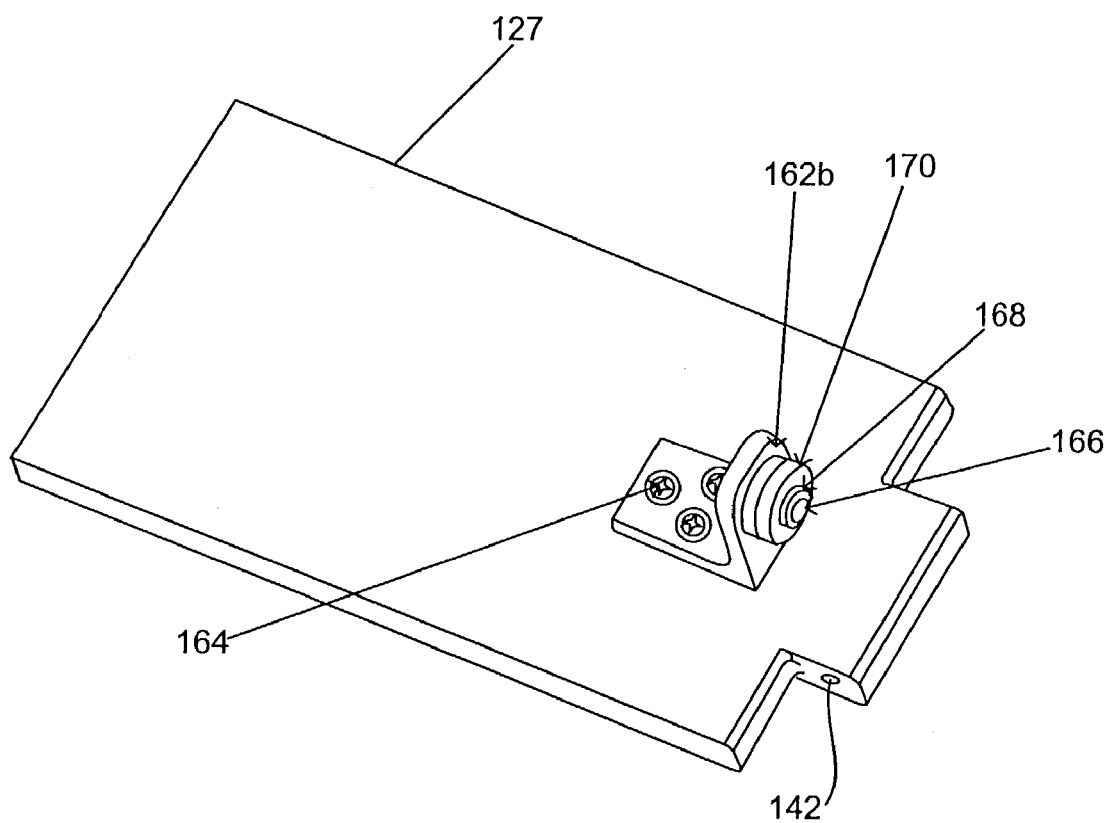
FIG. 2C illustrates a top prospective view of the door underside for the induction chamber of FIG. 1.
Figure 2D:
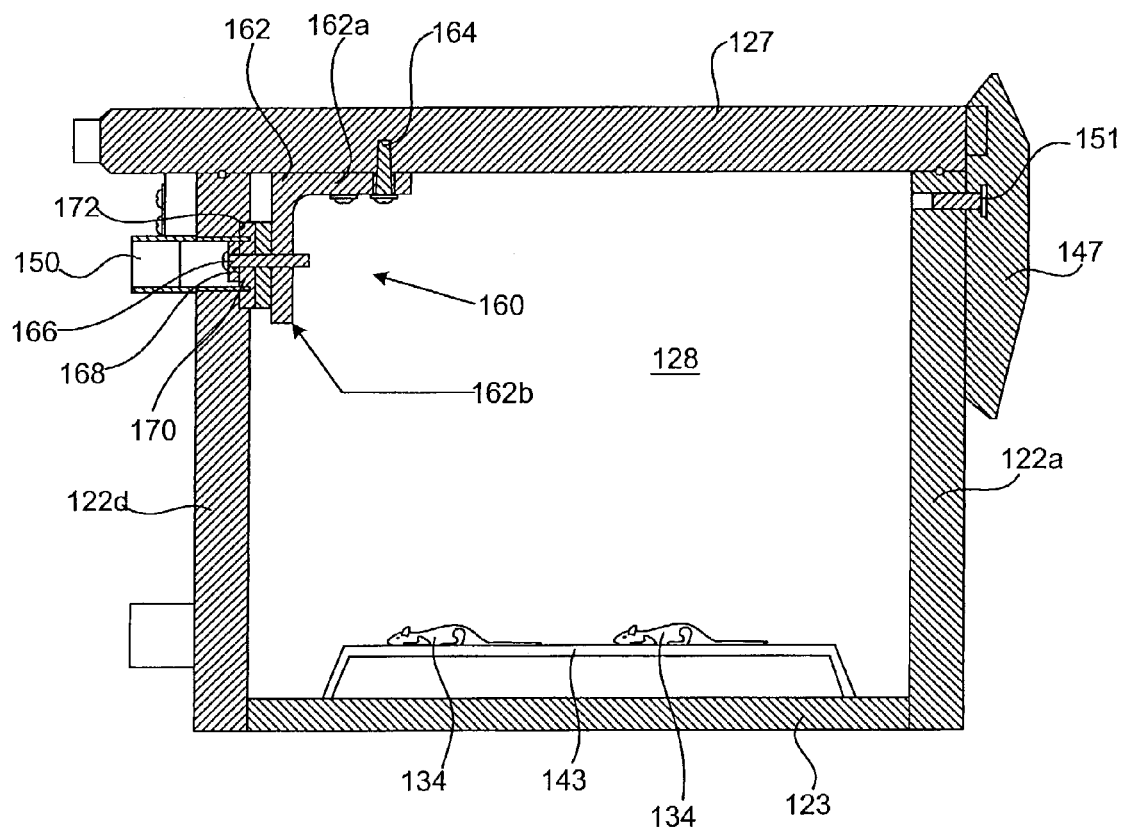
FIG. 2D illustrates a side cross sectional view of induction chamber of FIG. 1 taken through the lateral midpoint.

FIG. 2A illustrates a top prospective view of the front of induction chamber 54. FIG. 2B illustrates a top prospective view of the back of induction chamber 54. FIG. 2C illustrates a top prospective view of the underside of door 124. FIG. 2D illustrates a side cross sectional view of induction chamber 54 taken through the lateral midpoint of side walls 112a and 122d.

Referring initially to FIG. 2A, induction chamber 54 includes four vertical side walls 122a-d fixed to a bottom 123. Side walls 122a-d include front wall 122a, side wall 122b, side wall 122c, and back wall 122d. Side walls 122, bottom 123 and top wall 127 then comprise a set of walls that define an interior cavity 128 (FIG. 2D) within induction chamber 54. As shown in FIG. 2D, interior cavity 128 is sufficiently sized to receive multiple living specimens 134. A cavity volume of about 2 to about 8 liters is suitable for many induction chambers. In one embodiment, interior cavity 128 has a cavity volume of about 3 to about 4 liters. Interior cavity 128 may include a stage 143 or platform that the living specimens rest upon.

Side walls 122, bottom 123 and top wall 127 each comprise a transparent material that allows a user to view interior chamber 128. In a specific embodiment, lexan, a transparent plastic such as polycarbonate, or a transparent acrylic, are used for the walls of induction chamber 54. Using transparent walls for induction chamber 54 advantageously allows a user to view the interior of induction chamber 54. Walls for induction chamber 54 may very in thickness from about ⅛ inch thick to about 1 inch thick, for example.

Induction chamber 54 comprises a door or user access port that allows user access to interior cavity 128. As shown in FIG. 2A, induction chamber 54 comprises a door 127 that comprises the top wall of chamber 54 and spans the entire top surface area of induction chamber 54 as defined by side walls 122a-d. Door 127 is hingeably coupled to back wall 122d using a pin 144 (FIG. 2B) that passes through a channel 141 included in the hinges 125 (FIG. 2A) and a channel 142 included in door 127 (FIG. 2C). Hinges 125 are screwed to the outside of back wall 122d (FIG. 2B).

Door 127 is movable between a closed condition and various opened conditions. FIG. 2A illustrates the closed condition for door 127 and induction chamber 54. In the closed condition as shown, door 127 rests upon the top portion of walls 122 and seals interior cavity 128 from the environment exterior to induction chamber 54. In one opened condition, door 127 enables user access into interior chamber to insert or remove living specimens. In the opened conditions, door 127 enables gaseous communication, or gaseous flow, between interior cavity 128 and the environment exterior to induction chamber 54 through an opening. The size and profile of the opening will depend on the angle door 127 makes relative to its closed position as shown. Thus, when door 127 is initially opened from the position shown in FIG. 2A, a crack between the top portion of each side wall 122 in door 127 creates an opening that allows anesthesia gas and oxygen to flow between interior chamber 128 and the environment external to induction chamber 54.

Seal 145 is disposed in a recess that runs perimetrically about a top portion of each side wall 122 (FIG. 2B). As shown in FIG. 2A, seal 145 runs 360 degrees about the top opening of interior cavity 128. Seal 145 is a compressible material that prevents gaseous communication between interior cavity 128 and the environment exterior to induction chamber 54 when door 127 is in the closed condition. More specifically, when door 127 is in the closed position, the bottom surface of door 127 cooperates with seal 145 to prevent gaseous communication between interior cavity 128 and the environment external to induction chamber 54. In a specific embodiment, seal 145 comprises a rubber or silicone.

Clamp 147 is attached side wall 122a using screws 151. Clamp 147 allows a user to secure door 127 in the closed position. In addition, clamp 147 is vertically disposed such that securing clamp 147 provides a compressive force between the bottom surface of door 127 and seal 145.

Induction chamber receives low-pressure oxygen and anesthesia gas from console 52 and conduit 60. Induction chamber 54 thus includes at least one gas inlet capable of providing anesthesia gas to the interior cavity 128. As shown, induction chamber 54 includes a single gas inlet 130 that supplies both anesthesia gas and oxygen from the exterior of induction chamber 54 to the interior cavity 128. Gas inlet 130 is disposed in a lower portion of back wall 122d and includes a circular port or hole through back wall 122d that allows gaseous communication between the inside and outside of induction chamber 54. As shown, gas inlet 130 includes an exterior interface 123 (FIG. 2B) that receives conduit 60 (FIG. 1). Referring back to FIG. 1, console 52 provides a mixture of oxygen and anesthesia gas to induction chamber 54. This mixture is passed into induction chamber 54 through gas inlet 130. Console 52 includes controls that allow a user to turn on/off or vary the flowrate of oxygen and anesthesia gas provided to induction chamber 54. It is understood that induction chamber 54 may include multiple gas inlets. For example, one inlet may be dedicated to anesthesia gas was a second gas inlet is dedicated to oxygen supply.

The present invention employs an anesthesia gas to sedate living specimens. As the term is used herein, an anesthesia gas refers to any gas or agent that is used to induce any level of anesthetic state, unconsciousness, lack of awareness, or local or general insensibility to pain for a specimen interacting with induction chamber 54. The amount of anesthesia gas is typically determined by the control console 52 of FIG. 1. A vaporizer included in console 52 may be used to produce the anesthesia gas and add it to low-pressure oxygen. The output of the vaporizer typically comprises a controlled and variable gas mixture of life sustaining gases and anesthetizing gases. In a specific embodiment, isoflurane is added to low pressure oxygen by passing oxygen across a vaporizer that evaporates isoflurane. In this case, the low-pressure oxygen acts as a carrier for the isoflurane, which is added to the oxygen according to the physical characteristics of isoflurane liquid and its temperature. Although the present invention is primarily described with respect to using only a single anesthesia gas, isoflurane, it is understood that an anesthesia gas of the present invention may include multiple anesthesia gases, as one of skill in the art will appreciate.

Induction chamber 54 also comprises a gas outlet 150 capable of drawing anesthesia gas from interior cavity 128 when door 127 is in an opened condition. Gas outlet 150 is disposed in an upper portion of back wall 122d and includes a circular port or hole through back wall 122d that allows gaseous communication between the inside and outside of induction chamber 54. As shown, gas outlet 150 includes an exterior interface 152 (FIG. 2B) that receives conduit 79, which exhausts gases from induction chamber 54 to filter 81 (FIG. 1).

Gas outlet 150 actively draws and collects anesthesia gas from interior cavity 128, and actively draws and collects anesthesia gas from the environment external to induction chamber 54 when door 127 is in an opened condition. To do so, gas outlet 150 is in gaseous communication with a negative pressure supply such as vacuum pump 83 (FIG. 1). Vacuum pump 83 provides a negative pressure to gas outlet 150 that draws gases into outlet 150. In one embodiment, the negative pressure is negative relative to the pressure within interior chamber 128. In another embodiment, the native pressure is negative relative to the environment exterior to induction chamber 54. This creates a draft through any opening created by door 127 that causes air and anesthesia gas to be drawn from the external environment, to pass in through interior cavity 128, and into gas outlet 150. Thus, with suitable pressure from pump 83, anesthesia gases about to escape interior cavity 128 when door 127 opens may be drawn and collected by gas outlet 150 before they escape. In addition, anesthesia gases that have escaped interior cavity 128 may be drawn and collected by gas outlet 150 when door 127 is opened.

The flowrate of anesthesia gas and other gases through gas outlet 150 may vary. In one embodiment, gas outlet 150 draws gases from interior cavity 128 at a flowrate through gas outlet 150 greater than the volume of interior cavity 128 per minute. In a specific embodiment, gas outlet 150 draws gases from interior cavity 128 at a flowrate from about 0 L/min to about 8 L/min.

Induction chamber 54 also comprises a gas outlet obstruction 160 that varies flow of anesthesia gas from interior cavity 128 through gas outlet 150 based on the position of door 127. Typically, gas outlet obstruction 160 varies flow of anesthesia gas from interior cavity 128 by obstructing gas outlet 150 in some manner. Thus, gas outlet obstruction 160 may plug, cap, cork, block, prevents, or otherwise impair gas flow through gas outlet 150.

As shown in FIG. 2D, gas outlet obstruction 160 comprises a bracket 162 having a portion 162a that rests flat against the bottom side of door 127 and is attached to door 127 using screws 164. Bracket 162 also has a portion 162b that is positioned proximate to gas outlet 150 when door 127 is in the closed position. Attached to portion 162b is screw 166, washer 168, compressible material 170 and spacer 172. Screw 166 fastens washer 168, compressible material 170 and spacer 172 to portion 162b. Compressible material 170 interfaces with gas outlet 150 to seal the outlet 150 when door 127 is in the closed position. Thus, portion 162b is proximate to gas outlet 150 such that compressible material 170 seals the outlet 150 when door 127 is in the closed position. Together, portion 162b and perimeter material of gas outlet 150 combine to compress the compressible material 170 when door 127 is in the closed condition. FIG. 2D illustrates gas outlet obstruction 160 when door 127 is in the closed position. Here, gas outlet obstruction 160 restricts flow of anesthesia gas from interior cavity 128 through gas outlet 150. Washer 168 allows screw 166 to tighten without compressing a localized portion of compressible material 170. Spacer 172 allows a user to change the thickness of compressible material 170 or vary the force applied between portion 162b and the perimeter material of gas outlet 150 on compressible material 170.

In a simplified embodiment, gas outlet obstruction 160 simply comprises a compressible material that spans the entire back side of portion 162b of bracket 162. Similar to the previous case, the this simplified embodiment seals gas outlet 150 when door 127 is in the closed condition. In addition, the gas outlet obstruction 160 allows gas to flow from interior cavity 128 through gas outlet 150 when door 127 is in an opened condition.

In one embodiment, gas outlet 150 is disposed in the top half of a side wall 122. In this case, anesthesia gas is introduced near the bottom of induction chamber 54 and collects in interior cavity 128 when door 127 is closed. When door 127 opens, gas outlet 150 draws anesthesia gas from the top portion of interior cavity 128. As long as the flowrate through gas outlet 150 is not excessive, this may result in a temporary two layer gaseous formation within interior cavity 128. The top layer comprises gases that move toward gas outlet 150. The bottom layer comprises anesthesia gas and oxygen supplied by gas inlet 123. An advantage of this design is that even with door 127 opened for short periods of time, living specimens is disposed near the bottom of induction chamber 54 may not be entirely devoid of anesthesia gas.

In one embodiment, passive gas outlet 132 is disposed in back wall 122c. Passive gas outlet 132 passively exhausts anesthesia gas from interior cavity 128 based on positive pressure in interior cavity 128 relative to conduit 77. Typically, this occurs when door 127 is in the closed condition and gas outlet 150 is obstructed. In this case, continual anesthesia gas and oxygen supply into interior cavity 128 builds pressure within the interior cavity and causes passive gas flow through gas outlet 132. Gas outlet 132 is disposed in a lower portion of back wall 122d and includes a circular port or hole through back wall 122d that allows gaseous communication between the inside and outside of induction chamber 54. As shown, passive gas outlet 132 includes an exterior interface 129 (FIG. 2B) that receives conduit 77, which exhausts gases from induction chamber 54 to filter 78 (FIG. 1).

Figure 3:
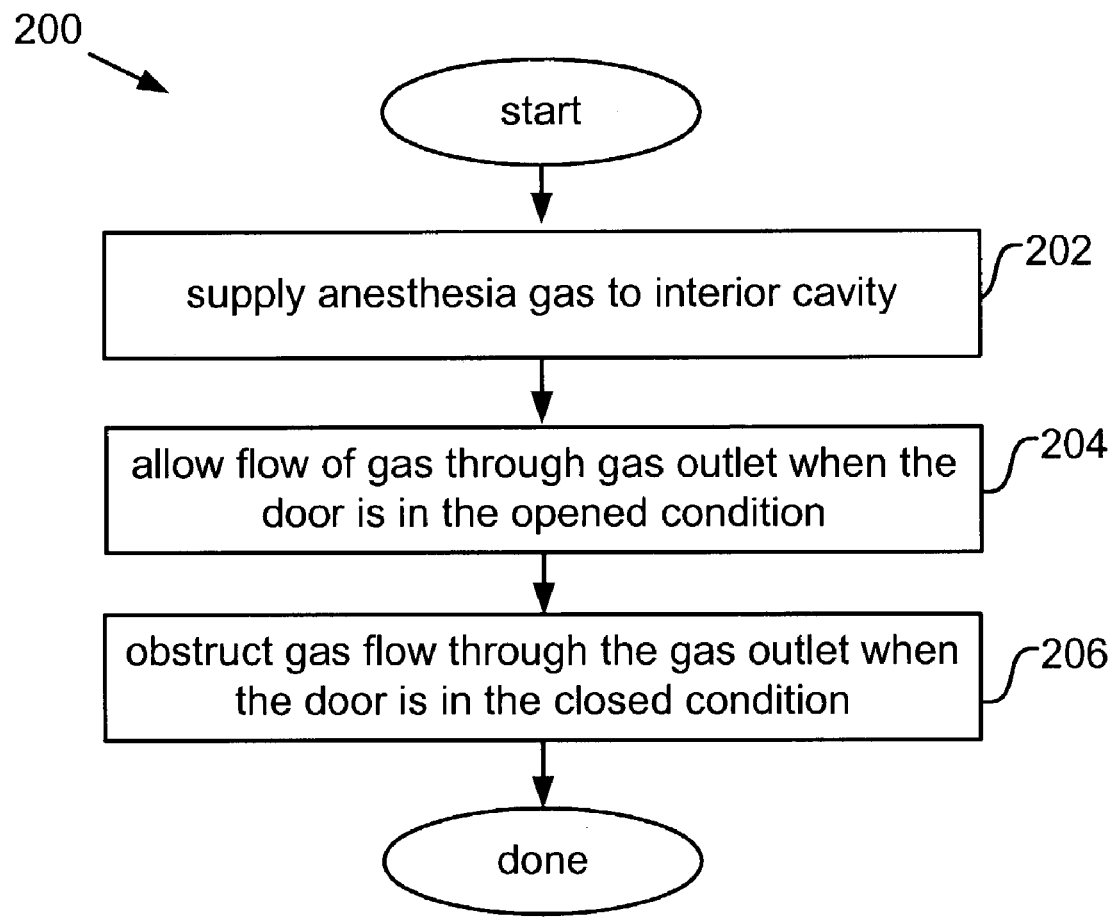
FIG. 3 illustrates a process flow for using the induction chamber of FIG. 1 in accordance with one embodiment of the present invention.

FIG. 3 illustrates a process flow 200 for using induction chamber 54 of FIG. 1 in accordance with one embodiment of the present invention. Processes in accordance with the present invention may include up to several additional steps not described or illustrated herein in order not to obscure the present invention.

In operation, a user opens door 127 (FIG. 1) and places a living specimen within the interior of induction chamber 54. Closing door 127 seals the interior of induction chamber 54 from the ambient room via the interface of seal 145 and door 127. In addition, a gas outlet obstruction obstructs gas flow through gas outlet 150 when door 127 is in the closed condition (206). In one embodiment, the gas outlet obstruction is attached to the door 127 and fully seals gas outlet 150 when door 127 is in the closed condition and fully prevents gas from flowing through gas outlet 150+.

After induction chamber 54 is sealed, oxygen and anesthesia gas are supplied to the interior via console 52 and gas inlet 130 (202). As pressure in the interior cavity builds, exhaust gases may be passively removed from induction chamber 54 via a passive exhaust included in induction chamber 54. Gas flows into the passive exhaust based on a positive pressure accumulating inside the chamber relative to the passive exhaust. After anesthesia delivery to the living specimen is complete, e.g. when the specimen has been anesthetized, door 127 may be opened to allow a lab technician to remove one or more specimens.

Opening door 127 ceases obstruction of gas outlet 150. This causes anesthesia gas to be drawn through gas outlet 150 from the interior chamber when door 127 is in the opened condition (204). In one embodiment, the gas outlet draws gases from the interior chamber at a flow rate greater than the volume of the interior chamber per minute. This is done with a negative pressure that is applied to the gas outlet, e.g., via a pump.

When used in the imaging system 10 of FIG. 1, process flow 200 may also include various additional actions related to imaging the specimen after it has been sedated. For example, a user may remove a living specimen from the interior cavity when the door is in the opened condition, place the living specimen in the imaging box, and image the living specimen, or a portion thereof, using the imaging system.

In early tests, induction chamber 54 produced improved results for its intended purpose when gas outlet 150 and obstruction 160 were used. In many cases, induction chamber 54 reduced the amount of anesthesia gas introduced into the ambient surroundings by a factor of about 4-5 relative to an induction chamber without an active gas outlet and gas outlet obstruction. In addition, opening door 127 did not result in frequent living specimen arousal—for both specimens being removed and resting temporarily while another specimen was being removed.

While this invention has been described in terms of several preferred embodiments, there are alterations, permutations, and equivalents which fall within the scope of this invention which have been omitted for brevity's sake. For example, although induction chamber 54 has been described with respect to an active gas outlet in a side wall, it is understood that other designs include the gas outlet in other positions such as a top wall. It is therefore intended that the scope of the invention should be determined with reference to the appended claims.

What is claimed is:

1. An induction chamber for delivering anesthesia gas to a living specimen, the chamber comprising:
   a set of walls defining an interior cavity;
   a door that is movable between an opened condition that enables gaseous communication between the interior cavity and the environment exterior to the induction chamber through an opening, and a closed condition that seals the interior cavity from the environment exterior to the induction chamber through the opening;
   a gas inlet disposed in one of the set of walls and capable of providing anesthesia gas to the interior cavity;
   a first gas outlet disposed in one of the set of walls and capable of drawing anesthesia gas from the interior cavity when the door is in the opened condition;
   a passive gas outlet disposed in one of the set of walls configured to passively exhaust anesthesia gas from the interior cavity based on positive pressure in the interior cavity when the door is in the closed condition; and a gas outlet obstruction that varies flow of anesthesia gas from the interior cavity through the first gas outlet based on the position of the door.

2. The induction chamber of claim 1 wherein the gas outlet obstruction allows gas to flow from the interior cavity through the first gas outlet when the door is in the open condition.

3. The induction chamber of claim 1 wherein the gas outlet obstruction prevents flow of anesthesia gas from the interior cavity though the first gas outlet when the door is in the closed condition.

4. The induction chamber of claim 3 wherein the gas outlet obstruction is attached to the door and seals the first gas outlet when the door is in the closed condition.

5. The induction chamber of claim 4 wherein the gas outlet obstruction comprises a compressible material that is compressed by interface with the first gas outlet when the door is in the closed condition.

6. The induction chamber of claim 1 wherein the door comprises a top wall for the set of walls.

7. The induction chamber of claim 1 wherein gases pass though the first gas outlet from the interior cavity at a flow rate greater than the volume of the interior chamber per minute.

8. The induction chamber of claim 1 wherein gases pass though the first gas outlet from the interior cavity at a flow rate from about 0 L/min to about 8 L/min.

9. The induction chamber of claim 1 wherein the first gas outlet is disposed in the top half of a vertical wall of the set of walls.

10. The induction chamber of claim 1 wherein the first gas outlet is in gaseous communication with a pump that provides negative pressure to the gas outlet.

11. The induction chamber of claim 10 wherein the negative pressure is negative relative to the environment exterior to the induction chamber.

12. The induction chamber of claim 1 further comprising a compressible seal that facilitates sealing of the interior cavity from the environment exterior to the induction chamber when the when the door is in the closed condition.

13. The induction chamber of claim 1 the set of walls comprise a transparent material that allows view of the interior chamber.

14. A method of using an induction chamber, the induction chamber comprising a set of walls that define an interior cavity and comprising a door that is movable between an opened condition and a closed condition, the method comprising:
supplying an anesthesia gas into the interior cavity;
drawing anesthesia gas through a first gas outlet disposed on one of the set of walls when the door is in the opened condition;
passively exhausting anesthesia gas from the interior cavity based on increased pressure in the interior cavity relative to a passive gas outlet when the door is in the closed condition; and
obstructing gas flow through the first gas outlet when the door is in the closed condition.

15. The method of claim 14 wherein the first gas outlet is sealed by a gas outlet obstruction attached to the door when the door is in the closed condition.

16. The method of claim 14 wherein the gases pass though the first gas outlet from the interior chamber at a flow rate greater than the volume of the interior chamber per minute.

17. The method of claim 16 wherein the gases pass though the first gas outlet from at a flow rate between about 0 L/min to about 8 L/min.

18. The method of claim 14 wherein the first gas outlet is disposed in the top half of a vertical wall of the set of walls.

19. The method of claim 14 further comprising applying negative pressure to the first gas outlet.

20. The method of claim 19 wherein a pump provides the negative pressure to the first gas outlet.

21. The method of claim 19 wherein the negative pressure is negative relative to the environment exterior to the induction chamber.

22. An induction chamber for delivering anesthesia gas to a living specimen, the chamber comprising:
a set of walls defining an interior cavity;
a door that is movable between an opened condition that enables gaseous communication between the interior cavity and the environment exterior to the induction chamber through an opening, and a closed condition that seals the interior cavity from the environment exterior to the induction chamber through the opening;
a gas inlet disposed in one of the set of walls and capable of providing anesthesia gas to the interior cavity;
a gas outlet disposed in one of the set of walls and capable of drawing anesthesia gas from the interior cavity when the door is in the opened condition; and
a gas outlet obstruction, attached to the door and comprising a compressible material that is compressed by interface with the gas outlet when the door is in the closed condition, that varies flow of anesthesia gas from the interior cavity through the gas outlet based on the position of the door, wherein the gas outlet obstruction seals the gas outlet and prevents flow of anesthesia gas from the interior cavity through the gas outlet when the door is in the closed condition.

23. The induction chamber of claim 22 wherein the gas outlet is disposed in the top half of a vertical wall of the set of walls.

* * * * *

UNITED STATES PATENT AND TRADEMARK OFFICE
CERTIFICATE OF CORRECTION

PATENT NO. : 7,331,341 B2  Page 1 of 1
APPLICATION NO. : 10/370031
DATED : February 19, 2008
INVENTOR(S) : Michael Bo Nelson It is certified that error appears in the above-identified patent and that said Letters Patent is hereby corrected as shown below:

In the Claims:

Claim 3, (Col. 11, line 10) change "though" to --through--.

Claim 7, (Col. 11, line 22) change "though" to --through--.

Claim 8, (Col. 11, line 26) change "though" to --through--.

Claim 16, (Col. 12, line 10) change "though" to --through--.

Claim 17, (Col. 12, line 13) change "though" to --through--.

Claim 17, (Col. 12, line 14) after "outlet" delete "from".

Signed and Sealed this

Second Day of December, 2008

JON W. DUDAS
*Director of the United States Patent and Trademark Office*